United States Patent [19]

Byrne et al.

[11] Patent Number: 4,590,284

[45] Date of Patent: May 20, 1986

[54] PINEAPPLE KETONE 1'-ALKOXYALKYL DERIVATIVES

[75] Inventors: Brian Byrne, Belleville, N.J.; Louise M. L. Lawter, Goshen, N.Y.

[73] Assignee: Hercules Incorporated, Wilmington, Del.

[21] Appl. No.: 728,540

[22] Filed: Apr. 29, 1985

Related U.S. Application Data

[63] Continuation-in-part of Ser. No. 627,311, Jul. 2, 1984.

[51] Int. Cl.$^4$ ............................................. C07D 307/60
[52] U.S. Cl. ................................... 549/477; 131/277; 252/522 R; 426/536
[58] Field of Search ........................................ 549/477

[56] References Cited

U.S. PATENT DOCUMENTS 3,455,702  7/1969  Willhalm et al. .................... 99/140
3,697,291  10/1972  Tonsbeek .............................. 99/107
3,983,885  10/1976  Demole ................................ 131/144
4,383,943  5/1983  Britten-Kelly .................. 252/522 R Primary Examiner—Richard L. Raymond
Attorney, Agent, or Firm—Dale R. Lovercheck

[57] ABSTRACT

A compound of the general formula,

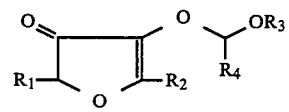

wherein $R_1$ and $R_2$ independently are —H, —CH$_3$, or —CH$_2$CH$_3$; and $R_3$ and $R_4$ are independently alkyl or alkenyl of from 1 to 10 carbons, or aryl of from 6 to 10 carbons, or $R_4$=hydrogen.

8 Claims, No Drawings

PINEAPPLE KETONE 1'-ALKOXYALKYL DERIVATIVES

This is a continuation-in-part of U.S. Ser. No. 627,311, filed July 2, 1984.

BACKGROUND OF THE INVENTION

This invention relates to flavors and specifically to modified pineapple ketone.

The prior art does not show the alkoxy alkyl ether dihydrofuranone compound of the invention. Nor is there a suggestion in the prior art of the substantial oxidative stability increases beneficially provided by the alkoxy alkyl ether dihydrofuranone compounds of the invention over the dihydrofurans and dihydrofuranones of the prior art.

Pineapple ketone is the common name for the chemical 2,5-dimethyl-4-hydroxy-3(2H)-furanone. This is a compound found in pineapples, strawberries, raspberries, meats, and other foods. It has been found in cooked, roasted and fermented foods including coffee, roasted filbert, roasted almond and soy sauce. Pineapple ketone is known to be formed by the non-enzymatic browning process that occurs during roasting and baking.

Because of its cotton-candy, caramelized-sugar flavor, pineapple ketone is used extensively to compound synthetic flavors. Pineapple ketone reacts readily with amines, aldehydes and oxygen. In such cases, the pineapple ketone content of the flavors is reduced, lowering the effectiveness of the flavor.

When pineapple ketone is used in chewing-gum, it is quickly "washed out" by the chewing process, resulting in rapid loss of flavor. This "washing out" effect is due to pineapple ketone being water soluble.

Willhalm et al., U.S. Pat. No. 3,455,702; Herman et al, U.S. Pat. No. 3,697,291; and Demole, U.S. Pat. No. 3,983,885 disclose that flavor may be imparted to foodstuffs, beverages, meat, or tobacco by incorporating therein a minor proportion of a dihydrofuran, such as, methyl and ethyl ethers.

Britten-Kelly, et al., U.S. Pat. No. 4,383,943, disclose that the 1'-ethoxyethyl ether of isoeugenol "retains the same odor characteristics as isoeugenol", unlike other cited derivatives. One of the advantages cited for the subject ether is that it is stable to discoloration in fragranced soaps after six months of storage, unlike isoeugenol which causes discoloration.

S. Arctander, "Perfume and Flavor Chemicals", published by the author, Montclair (1969), describes the use of numerous 1'-alkoxyalkyl ethers as useful for flavor and fragrance compositions. Several examples are shown below:

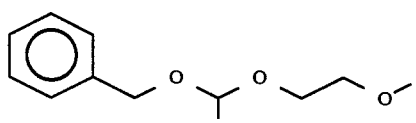

Compound 4

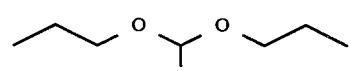

Compound 9

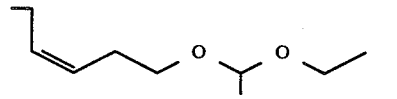

Compound 10

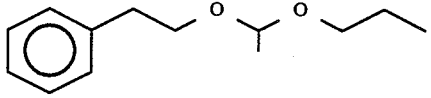

Compound 12

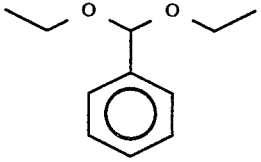

Compound 269

SUMMARY OF THE INVENTION

A new pineapple ketone 1'-alkoxyalkyl ether of the general formula,

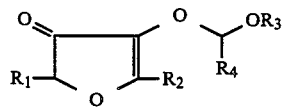

wherein $R_1$ and $R_2$ independently are —H, —CH$_3$, or —CH$_2$CH$_3$; and $R_3$ is alkyl of from 1 to 10 carbons, alkenyl of from 1 to 10 carbons, or aryl of from 6 to 10 carbons. $R_4$ is hydrogen, alkyl of from 1 to 10 carbons, alkenyl of from 1 to 10 carbons or aryl of from 6 to 10 carbons.

The invention solves the wash out problems associated with the use of pineapple ketone, while extending the flavor over a longer period of time. By reacting pineapple ketone with ethyl vinyl ether or other 1-alkoxy-1-alkenes with trace acid catalyst, the new and improved pineapple ketone derivatives are formed.

DETAILED DESCRIPTION OF THE INVENTION

The invention relates to new 1'-alkoxy alkyl ethers derived from pineapple ketone. By forming the new derivatives, the chemical reactivity of the resulting compounds is unexpectedly reduced compared with pineapple ketone; however, the flavor of the derivatives remains very similar to the flavor of pineapple ketone. This allows direct replacement of the new derivatives in applications where pineapple ketone is normally used. Additionally, the increased oxidative stability of these derivatives over pineapple ketone allow their use in applications where pineapple ketone cannot be used or does not perform well. Such applications include but are not limited to perfumes, dry flavors and tobacco.

Furthermore, the new compounds are not as water soluble as pineapple ketone, which allows these derivatives to be preferentially dissolved by chewing- or bubble-gum base. This effect allows the compounds to liberate pineapple ketone-like flavor slowly during the duration of the chew, creating a flavor prolongation effect.

The method of making the ether compounds of the invention involves the heretofore unknown reaction of ketones and diones with 1-alkoxy-1-alkenes to form enol ethers.

Unexpectedly, the compounds of the invention are more stable to oxidation than pineapple ketone. Hirvi, et al., (Lebensm.-Wiss. u.-Technol., 13, 324 (1980)) have indicated how sensitive pineapple ketone is to oxidation. At pH 4, it has a half-life of 120 days, while at pH 7, it has a half-life of 12 days. The increased oxidative stability of the novel compounds of the invention over pineapple ketone is shown in Example 3. An unexpected aspect of this invention is that the compounds of the invention have a similar taste to pineapple ketone.

The compounds of the invention offer the following advantages:

(a) The new compounds have flavor properties similar to pineapple ketone;
(b) The new compounds offer oxidative stabilities superior to pineapple ketone, allowing them to be used in situations where pineapple ketone will be unstable. Such situations include liquid flavors, and especially, dry flavors;
(c) The new compounds can be used in perfumes, whereas pineapple ketone is unstable leading to changes in the fragrance profile over time and discoloration of the formulation;
(d) The new compounds prolong flavor in chewing-gum and bubble-gum.

Exemplary of the preferred extended flavor compounds of the invention are:

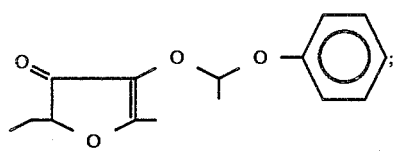

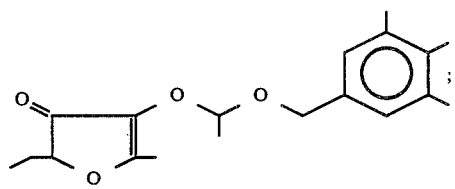

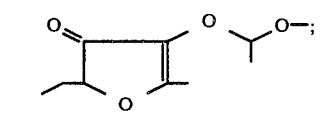

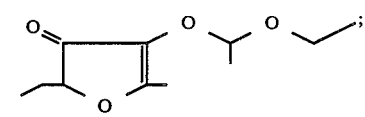

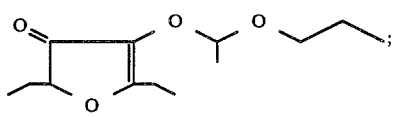

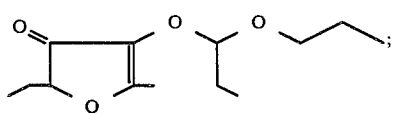

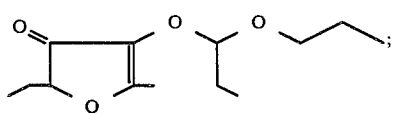

-continued

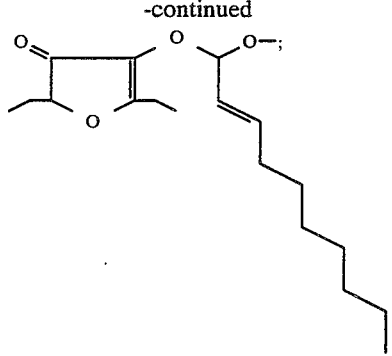

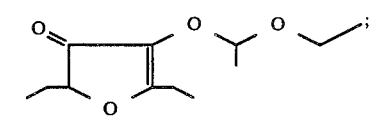

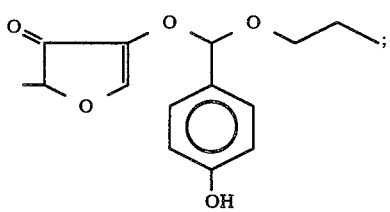

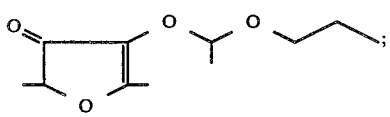

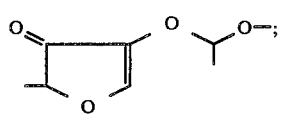

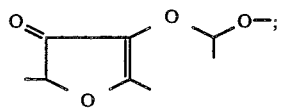

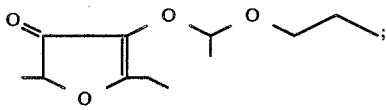

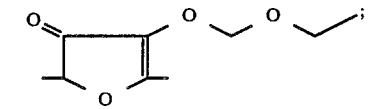

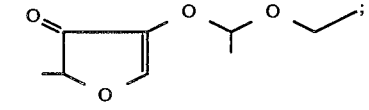

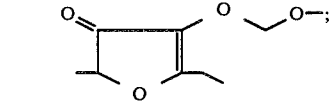

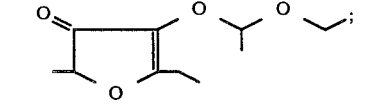

-continued

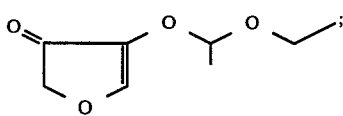

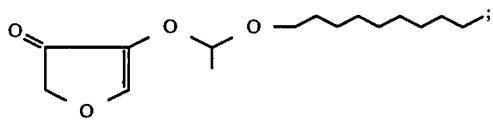

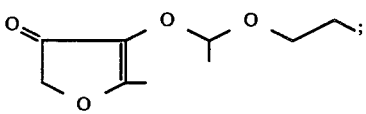

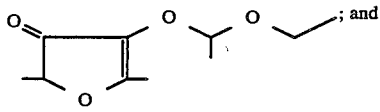 ; and

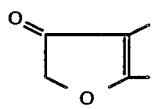

Exemplary of the other preferred compounds of the invention are:

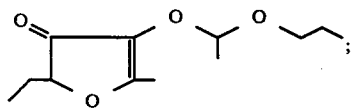

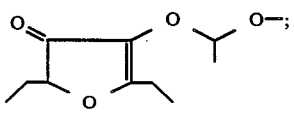

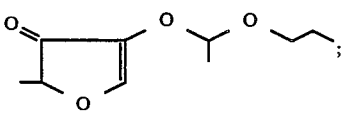

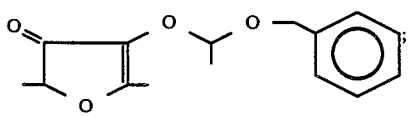

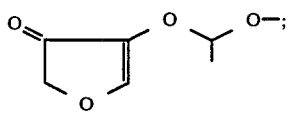

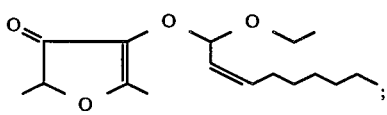

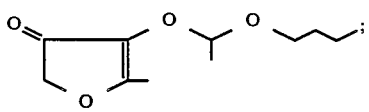

-continued

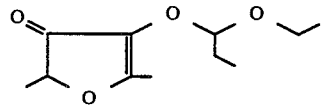

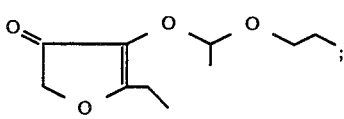

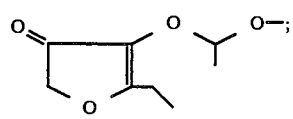

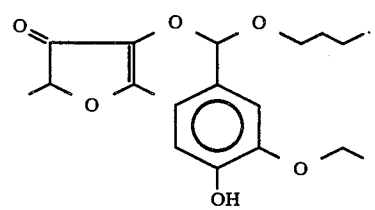

EXAMPLE 1

Preparation of 2,5-Dimethyl-4-[(1'-ethoxy)ethoxy]-3(2H)-furanone

To a heterogenous solution of 2,5-dimethyl-4-hydroxy-3-(2H)-furanone (133.0 g, 1.0 mole) and ethyl vinyl ether (144.0 g, 2.0 moles) at 10° C., under $N_2$, is added dropwise, concentrated hydrochloric acid (1.0 g). The temperature rises to 11° C. and the solution becomes homogeneous. It is stirred for 1.5 hours, and then the coolant is removed. Stirring is continued at room temperature for an additional six hours, after which the reaction is quenched by the addition of solid sodium bicarbonate (10 g, 0.12 mole). The reaction mixture is washed with 100 ml water and a second time with 100 ml of 5% $NaHCO_3$. The product is dried over $Na_2SO_4$ and distilled to give a 78.9% yield (161.8 g) of 2,5-dimethyl-4-[(1'-ethoxy)ethoxy]-3(2H)-furanone, b.p. 91° C. (0.05 torr), IR (neat, film) 1200, 1625, 1700, 2030, 2978 cm$^{-1}$; $^1$H NMR (CDCl$_3$) δ1.20 (t, J=8 Hz, 3), 1.32 (d, J=5 Hz, 3), 1.42 (d, J=7 Hz, 3), 2.2 (S, 3), 3.72 (m, 2), 4.48 (q, J=7 Hz, 1), 5.32 (q, J=5 Hz, 1).

EXAMPLE 2

Preparation of 2,5-Dimethyl-4-[(1'-butoxy)ethoxy]-3(2H)-furanone 2,5-Dimethyl-4-hydroxy-3(2H)-furanone (13.3 g, 0.1 mole) and butyl vinyl ether (20.0 g, 0.2 mole) are reacted as in Example 1 to give a 37.8% yield (8.83 g) of 2,5-dimethyl-4-[(1'-butoxy)ethoxy]-3(2H)-furanone, b.p. 68.8° C. (0.75 torr) IR (neat, film) 1200, 1625, 1700, 2865, 2930, 2958, 2978 cm$^{-1}$, $^1$H NMR (CDCl$_3$) δ0.95 (m, 3), 1.35 (d, J=5 Hz, 3), 1.38 (d, J=8 Hz, 3), 2.18 (S, 3), 3.70 (m, 2), 4.48 (q, J=7 Hz, 1) 5.31 (q, J=5 Hz, 1).

EXAMPLE 3

Oxidative Stability of Pineapple Ketone and the Product of Example 1

The comparative stability of pineapple ketone and the 1'-ethoxyethyl pineapple ketone derivative product of Example 1 are shown below. The disappearance of both compounds is measured by gas chromatography using a six foot long, one-eighth inch diameter column having 15 percent by weight polyethylene glycol with an average molecular weight of 20,000 (Carbowax-20 M, Trademark) on particles of 80 by 100 mesh diatomaceous earth (Chromasorb W, Trademark) and using helium feed at 28 cc. per minute while heating from 100° to 210° C. at 8° per minute. Ten percent solutions of each compound in toluene are stirred at equal rates in the presence of air at ambient temperatures.

|  Pineapple Ketone | | 2,5-Dimethyl-4[(1'-ethoxy)ethoxy]-3(2H)-furanone | |
| --- | --- | --- | --- |
| Time (Hours) | % Remaining | Time (Hours) | % Remaining |
| 0 | 100 | 0 | 100 |
| 15 | 24 | 17 | 95 |
| 41 | 18 | 41 | 93 |
| 115 | 6 | 116 | 44 |
| 138 | 4 | 137 | 38 |

EXAMPLE 4

Bubble Gum

A typical bubble gum base is made with the following ingredients:

| | |
| --- | --- |
| Bubble Base T, Acid Balance (a gum base) (L. A. Dreyfus Co., South Plainfield, NJ) | 135.00 parts |
| Corn Syrup, 43° baume | 161.25 parts |
| Powdered sugar, confectioners 10X | 450.00 parts |
| Citric acid | 3.75 parts |
| Glycerine | 3.75 parts |

All of these ingredients are mixed in a gum blender with a jacketed sidewall. Gum A is formed by mixing 7.50 parts strawberry flavor 500389-U (Hercules, PFW Division, Middletown, NY) with the above parts of bubble gum base. Gum B is formed by mixing 7.30 parts strawberry flavor 500389-U, plus 0.20 parts of 2,5-dimethyl-4-[(1'-ethoxy)ethoxy]-3(2H)-furanone with parts of bubble gum base. The gums are cut into 5.0 gram pieces and evaluated by panelists. Both gums A and B have a long-lived strawberry flavor, with gum B having a higher overall rating for flavor prolongation after 10 minutes, as well as, having a higher and more sustained flavor intensity peak during the middle of the chew. Gum B is judged to have best retained the strawberry character throughout the chew.

Other features, advantages and specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. A compound of the general formula,

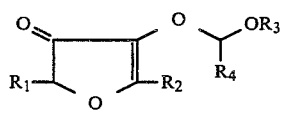

wherein $R_1$ and $R_2$ independently are -H, -CH$_3$, or -CH$_2$CH$_3$; and $R_3$ is alkyl of from 1 to 10 carbons, alkenyl of from 1 to 10 carbons, or aryl of from 6 to 10 carbons, $R_4$ is hydrogen, alkyl of from 1 to 10 carbons, alkenyl of from 1 to 10 carbons or aryl of from 6 to 10 carbons.

2. The compound of claim 1 having the formulas:

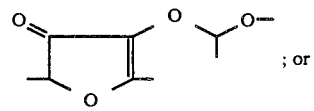

; or

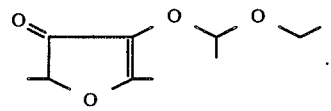

3. The compound of claim 1 having the formulas:

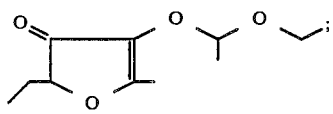

;

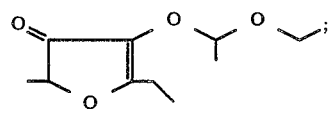

;

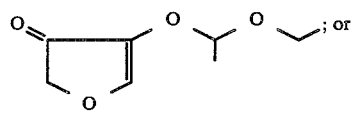

; or

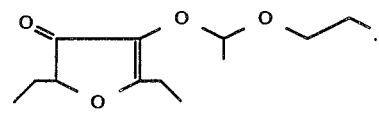

.

4. The compound of claim 1 having the formulas:

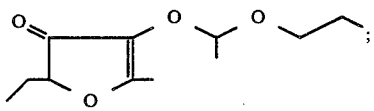

;

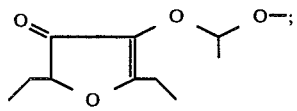

;

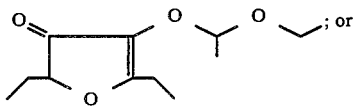

; or

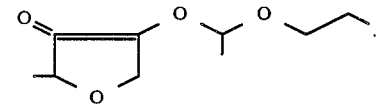

.

5. The compound of claim 1 having the formulas:

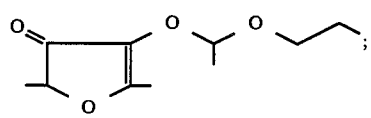
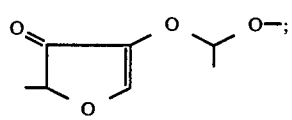
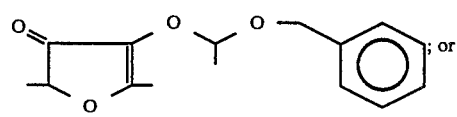
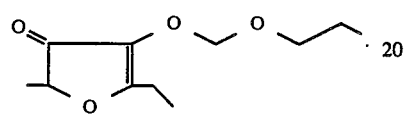
6. The compound of claim 1 having the formulas:
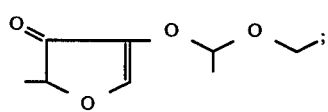
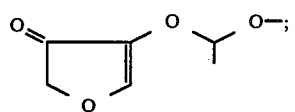
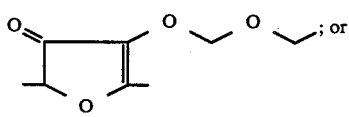
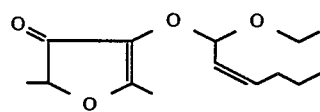
7. The compound of claim 1 having the formula:
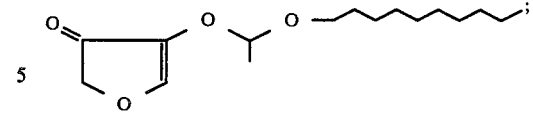
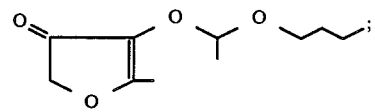
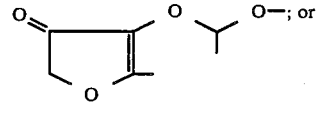
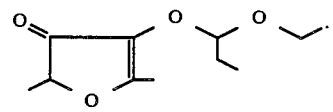
8. The compound of claim 1 having the formulas:
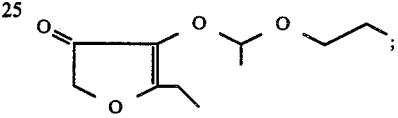
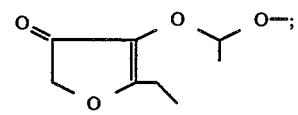
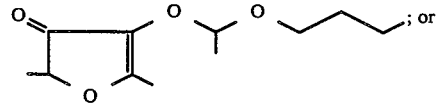
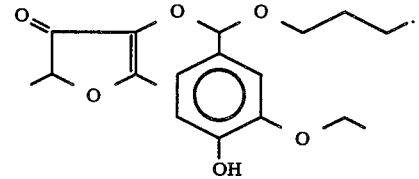
* * * * *

UNITED STATES PATENT AND TRADEMARK OFFICE
CERTIFICATE OF CORRECTION

PATENT NO. : 4,590,284
DATED : May 20, 1986
INVENTOR(S) : Brian Byrne & M. L. Lawter It is certified that error appears in the above-identified patent and that said Letters Patent are hereby corrected as shown below:

Column 6, Line 45  "  2030  "

Should read  --  2930  --

Column 8, Between Lines 63 - 66  " 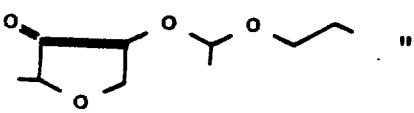 "

Should read  -- 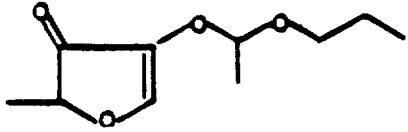 --

Signed and Sealed this

Second Day of September 1986

[SEAL]

Attest:

DONALD J. QUIGG

Attesting Officer    Commissioner of Patents and Trademarks